United States Patent [19]

Grassman et al.

[11] Patent Number: 5,017,620

[45] Date of Patent: May 21, 1991

[54] PESTICIDE COMPOSITION

[75] Inventors: David L. Grassman, Issaquah; Scott P. Ager, Seattle; Tamis L. Root, Yakima, all of Wash.

[73] Assignee: E. M. Matson, Jr., Company, Inc., Seattle, Wash.

[21] Appl. No.: 392,051

[22] Filed: Aug. 10, 1989

[51] Int. Cl.$^5$ ...................... A01N 35/00; A01N 35/02
[52] U.S. Cl. ................................... 514/698; 514/696; 514/693; 424/84
[58] Field of Search .................. 424/410, 84; 514/698, 514/696, 693

[56] References Cited

U.S. PATENT DOCUMENTS

| | | | |
|---|---|---|---|
| 2,363,852 | 11/1944 | Beekler | 167/48 |
| 2,504,207 | 4/1950 | Littler | 167/53.2 |
| 2,778,768 | 1/1957 | Brown et al. | 167/42 |
| 2,875,834 | 3/1959 | Shumard | 167/22 |
| 2,952,689 | 9/1960 | Enders et al. | 260/343.2 |
| 2,988,473 | 6/1961 | Mallis et al. | 167/27 |
| 3,005,751 | 10/1961 | Stansbury | 167/38.6 |
| 3,058,880 | 10/1962 | Muller et al. | 167/33 |
| 3,090,723 | 5/1963 | Pastac | 167/46 |
| 3,132,067 | 5/1964 | Rauscher et al. | 167/14 |
| 3,238,092 | 1/1966 | Boyce et al. | 167/30 |
| 3,458,639 | 7/1969 | Heiss et al. | 424/300 |
| 3,544,677 | 12/1970 | Lapham et al. | 424/17 |
| 3,663,707 | 5/1972 | Montagne et al. | 424/300 |
| 3,740,201 | 6/1973 | Woodruff | 260/29.7 M |
| 3,816,610 | 6/1974 | Lusby | 424/17 |
| 4,011,332 | 3/1977 | Schoetensack et al. | 424/273 |
| 4,156,780 | 5/1979 | Kilbourn et al. | 546/330 |
| 4,184,866 | 1/1980 | Dellicolli et al. | 71/65 |
| 4,762,718 | 8/1988 | Marks, Sr. | 424/409 |
| 4,765,979 | 8/1988 | Nielsen | 424/84 |
| 4,826,685 | 5/1989 | Stewart | 424/410 |

FOREIGN PATENT DOCUMENTS

| | | |
|---|---|---|
| 383009 | 5/1987 | Austria . |
| 0115664 | 8/1984 | European Pat. Off. . |
| 1498299 | 10/1967 | France . |
| 1575437 | 7/1969 | France . |
| WO82/00237 | 2/1982 | PCT Int'l Appl. . |
| 498498 | 2/1939 | United Kingdom . |
| 1033692 | 6/1966 | United Kingdom . |
| 2081583 | 2/1982 | United Kingdom . |

OTHER PUBLICATIONS

Chemical Abstracts (72: 120496z) 1970.
Chemical Abstracts (107: 72911y) 1987.

*Primary Examiner*—Shep K. Rose
*Assistant Examiner*—Kevin Weddington
*Attorney, Agent, or Firm*—Christensen, O'Connor, Johnson & Kindness

[57] ABSTRACT

Water-based pesticide compositions are disclosed that are effective to kill molluscs, insects, and small rodents. The compositions are resistant to washing away by water, yet retain moisture such that the texture of the composition is such that pests find it palatable even after extended periods of time have passed after application. The compositions are environmentally safe and do not pose a significant toxicological threat to humans and pets.

27 Claims, No Drawings

PESTICIDE COMPOSITION

TECHNICAL FIELD

The present invention relates to pesticide compositions, particularly pesticide compositions effective for controlling the population of molluscs such as slugs and snails.

BACKGROUND OF THE INVENTION

Slugs and snails are capable of causing substantial damage to ornamental plants and agricultural crops. Slugs and snails are omnivorous and find leaves, bulbs, tubers, fungi, ligands, algae and animal matter very attractive for consumption. Agricultural crops such as leafy vegetables, green beans and strawberries can be extensively damaged by molluscs. Also fruit and fruit trees can be extensively damaged by the foraging creatures. Livestock feed crops, such as hay and clover can also be extensively damaged by molluscs. Tests have shown that a slug or snail can consume its own weight in food in a matter of days. In addition to damaging or killing plant life, many homeowners find the physical appearance of slugs and snails objectionable.

If uncontrolled, slugs and snails can reproduce rapidly, resulting in an exponential increase in damage to horticultural and agricultural plant life. Because slugs and snails are semi-nocturnal, they often avoid capture by their natural predators, including birds, that generally actively feed only during the daylight hours.

The substance metaldehyde has been used to control slug and snail populations. When the slugs or snails either ingest or contact metaldehyde, the metaldehyde induces a brief period of paralysis followed by stimulation of the mucous secreting glands in the slugs or snails. Such stimulation of the mucous secreting glands results in the production of excessively large quantities of a viscid slime. Excessive slime production, in combination with the desiccating effect of exposure to sunlight during daylight hours causes the slugs to die by dehydration. Known molluscicides to control slug and snail populations commonly combine metaldehyde or another composition lethal to molluscs with a dry particulate material that serves to carry the poison and/or act as an attractant for the slugs and snails. Alternatively, the poison and particulate material are formed into pellets for convenient application. Such known molluscicides, commonly known as dry bait, suffer from several disadvantages. For example, water from precipitation or irrigation tends to wash away or dilute the bait at the point of application. In addition, the water can cause the poison to become detached from the carrier material and be washed into the soil where it will not be effective against snails and slugs unless they burrow into the soil and come into contact with or ingest the poison. Also, if the dry bait is applied under relatively low humidity conditions or low moisture conditions, it can be blown away. Finally, because the carrier for the poison is often an organic material, when exposed to moisture and heat at the point of application, the organic material tends to mold and decompose, leaving an unsightly residue.

Weatherproof types of baits or poisons have been developed. For example, in U.S. Pat. No. 2,363,852, finely divided metaldehyde is distributed throughout a weatherproof or weather resistant body produced from paraffin oil. The '852 patent also describes that various attractants can be added to the combination of the paraffin oil and metaldehyde. Another type of weatherproof poison includes an oil-based emulsion as a vehicle for delivering the poison to the point of application. Unfortunately, previous weatherproof types of baits are either less effective than desired and/or still susceptible to erosion by water during extended periods of precipitation or irrigation. Further, the oil-based carriers can be difficult to handle during production and tend to lose their palatable texture after extended periods of exposure to outdoor conditions. Finally, weatherproof types of baits that employ oil-based carriers introduce hydrocarbon derivatives into the environment as the bait erodes.

It would be desirable to provide a weatherproof type of pesticide composition that kills pests effectively without endangering other types of plant and animal life that may come into contact with the pesticide. The pesticide composition should be resistant to environmental conditions, such as water and wind, and yet should be safe to introduce into the environment.

SUMMARY OF THE INVENTION

A pesticide composition formed in accordance with the present invention effectively kills pests and is highly resistant to erosion when contacted with water, yet retains moisture so that the composition continues to be attractive to and edible by the pests even after extended periods of exposure to outdoor conditions. The pesticide composition includes an aqueous carrier, a poison in an amount effective to kill the pests that ingest or contact the composition, an attractant for the pests, a thickener for increasing the viscosity of the pesticide composition such that the pesticide composition is flowable and will remain in place after application, and a humidifying agent to promote retention of moisture in the composition.

Pesticide compositions formed in accordance with the present invention effectively control the population of pests, such as slugs and snails, for extended periods of time even after repeated contact with water in the form of precipitation or irrigation. The composition also maintains a texture that is attractive to the pests even after repeated exposure to water, sunlight and other outdoor conditions.

DETAILED DESCRIPTION OF THE INVENTION

The following description of pesticide compositions formed in accordance with the present invention is in the context of a composition fatal to molluscs such as slugs and snails. It should be understood that pesticide compositions formed in accordance with the present invention would also be effective for controlling other pests, such as small rodents or insects, by manipulating the type of poison and its concentration, something that should be within the scope of technical knowledge possessed by one skilled in the art of pest control.

In the context of molluscs, the pesticide composition formed in accordance with the present invention includes an aqueous carrier, preferably water. Water is a major component of a pesticide composition formed in accordance with the present invention and is generally present in an amount that in combination with the balance of the components described hereinbelow provides a pesticide composition that is flowable when dispensed, yet will remain in place after application. Generally, water is present in an amount ranging from about 70.0 to about 80.0 weight percent (wt. %) based on the total weight of the pesticide composition. Because some of the other components are water insoluble, a pesticide composition formed in accordance with the present invention is not a truly homogenous mixture but more accurately is a uniform dispersion of water insoluble components within a water base.

The poison that is used in pesticide compositions formed in accordance with the present invention can be selected from those compositions that are known to be lethal to the pest to be controlled, yet can be safely introduced into the environment without significant risk to the well being of other organisms. In the context of a molluscicide composition, the poison can be metaldehyde, 3,5-dimethyl-4-(methylthio)phenyl methylcarbamate, 4-(dimethylamino)-3,5-dimethylphenolmethyl carbamate, 3,5-dimethyl-4-(methylthio)phenolmethyl carbamate, N-tritylmorpholine-5,2-dichloro-4-nitrosalicylanilide, S-methyl-N-(methylcarbamoyl)oxythioacetimidate, calcium arsenate, or combinations of the above. It should be understood that the specific poisons listed above are intended as examples of the many poisons that are known to be lethal to molluscs. In the context of a poison for insects, any of the well known insecticides such as carbaryl (1-napthyl-N-methyl carbamate) available under the trademark SEVIN TM from Rhone-Poulenc, Research Triangle, N.C., that are environmentally safe may be used in accordance with the present invention. For small rodents, poisons such as zinc phosphide, 3-(α-acetonylbenzyl)-4-hydroxycoumarin available under the trademark WARFARIN TM from the Velsicol Chemical Corporation, Chicago, Ill., 2-diphenylacetyl-1,3-indandione, 2-diphenylacetyl-1,3-indandione, and chlorophacinone and mixtures thereof are known to be lethal to small rodents. In the context of a pesticide composition for molluscs, the poisons can be used in an amount ranging from about 2.0 to about 10.0 wt. % based on the total weight of the pesticide composition. Preferably, the poison for molluscs is metaldehyde used in an amount that ranges from about 3.0 to about 6.0 wt. % based on the total weight of the pesticide composition. For pesticide compositions lethal to other non-mollusc pests, the specific amount of poison used will depend upon the poison's toxicity to the rodent or insect to be controlled.

The attractant that is used in a pesticide composition formed in accordance with the present invention can generally be any material that is easily dispersed in the water carrier and which the pests find attractive. For molluscs, the attractant can be a vegetable, grain, fruit, animal or fish meat or any derivatives of the above materials that molluscs generally find attractive. Particular examples of vegetables or vegetable derivatives include peas, carrots, lettuce, cabbage, potatoes, celery, and the like. Alfalfa, wheat, oats, barley, malt, beer mash, rye, and corn are examples of grains or grain derivatives that molluscs find attractive. Examples of fruit products and their derivatives that molluscs find attractive include apples, pears, peaches, prunes, apricots, grapes, and the like. Animal or fish meats can be used in either a cooked form or a raw form. Prior to mixing with the water carrier, the attractant should be reduced to a fine powder or paste suitable for uniform dispersion throughout the aqueous carrier. For molluscs, the preferred attractant is malt extract. The attractant can be used in an amount ranging from about 3.0 to about 10.0 wt. % based on the total weigh of the pesticide composition, although amounts outside this range can also be used.

Depending upon the relative amounts of the other components in the pesticide compositions formed in accordance with the present invention, a thickener material is generally required in order to increase the viscosity of the pesticide composition such that the pesticide composition will flow for application and remain in place after application. The thickness of the pesticide composition should be such that it can be dispensed from a substantially airtight squeeze bottle through an orifice producing a string of the pesticide composition by applying pressure to the outside of the bottle. Generally, the composition should be capable of being caused to flow through an orifice having a diameter ranging from about 2 to 8 millimeters by increasing the pressure within the otherwise substantially airtight bottle. It should be understood that the viscosity of the pesticide composition formed in accordance with the present invention will be such that the pesticide composition can be made to flow through smaller or larger orifices. The size of the orifice in the squeeze bottle will be determined by the desired amount of the pesticide composition to be applied at the point of application, taking into consideration the pressure exerted by the user on the bottle and the period of time the pressure is exerted. In order to ensure that the composition remains in place after application, the viscosity of the pesticide composition should also be such that when applied to a horizontal surface, the composition is non-leveling. In other words, when applied to a horizontal surface, a string of pesticide composition formed in accordance with the present invention does not tend to flatten out over the horizontal surface. Increasing the viscosity of the pesticide composition so it will remain in place after application must be weighed against the need to provide a composition that will flow when pressure is applied (e.g., upon dispensing).

Generally, the consistency of a pesticide composition formed in accordance with the present invention can be described as being similar to mayonnaise. Examples of suitable thickeners include starches, gums, casein, gelatin, phycocolloids, semi-synthetic cellulose derivatives such as carboxymethylcellulose and the like, polyvinyl alcohol, carboxyvinylates, bentonite, silicates, and colloidal silica. Specific examples of thickeners include sodium alginate, potassium alginate, calcium alginate, propylene glycol alginate, fused silica, talc, magnesium aluminum silicate, xanthan gum, bentonite clay, corn starch, potato starch, soy starch, wheat starch, or any combinations of the above. Preferably, xanthan gum, bentonite clay, or corn flour are used as the thickening agent for the pesticide composition formed in accordance with the present invention. The thickeners are used in an amount effective to provide a pesticide composition having a viscosity ranging between about 6,000 centipoise to about 18,000 centipoise at 20° C. Preferably, the viscosity of the pesticide composition ranges from about 8,000 centipoise to about 10,000 centipoise at about 20° C. In order to achieve a viscosity within the ranges described above, a preferred thickening composition is used in an amount ranging from about 3.0 to about 15.0 wt. % based on the total weight of the pesticide composition. Preferably, the preferred thickening agents are used in an amount ranging from about 5.0 to 10.0 wt. % based on the total weight of the pesticide composition.

The humidifying agent serves to stabilize the moisture content of pesticide compositions formed in accordance with the present invention during storage and after application. The humidifying agent may absorb minimal amounts of moisture after the pesticide composition has been dispensed at the point of application. Specifically, the humidifying agent helps to retain the moisture that is originally present in the pesticide composition after the pesticide composition is dispensed at the point of application or otherwise removed from its storage container. One reason for stabilizing the moisture content of the pesticide compositions formed in accordance with the present invention is to maintain the texture of the compositions in a state that is palatable to the pests. The palatable nature of the pesticide compositions formed in accordance with the present invention refers to a softness of texture that enables molluscs or other pests to readily ingest or come into intimate contact with the composition. It is preferred to keep the compositions palatable to the pests for as long as possible in order to extend the period of time between applications by extending the effective lifetime of the pesticide composition. Once the compositions lose a substantial amount of their original moisture they tend to dry out and become "crunchy" or have a texture somewhat like burlap. In this dried out state the pests do not find the pesticide as attractive for ingestion. Also, especially with molluscs, when the pesticide composition is in a dried out state, the poison is not as readily transferred to the molluscs upon contact compared to when the pesticide composition contains most of its original moisture.

Examples of humidifying agents or humectants that are useful in the pesticide composition formed in accordance with the present invention include polyhydric alcohols such as glycerol, d-sorbitol (sorbitol), and POLYOL-P TM available from Pfizer, Inc. Generally, the humidifying agent should be used in an amount effective to promote the retention of moisture in the pesticide composition after application. The amount of humidifying agent used in a pesticide composition formed in accordance with the present invention can range from about 2.0 to about 10.0 wt. % based on the total weight of the pesticide composition. Preferably, in the context of a molluscicide, the humidifying agent is d-sorbitol used in an amount ranging from about 3.0 to about 5.0 wt. % based on the total weight of the pesticide composition.

Optional ingredients for pesticide compositions formed in accordance with the present invention include a preservative to retard mold growth and decomposition of the pesticide compositions. Examples of suitable preservatives include sodium benzoate, potassium sorbate, formaldehyde, a cosmetic grade preservative sold under the name DANTOGARD TM available from Lonza AG, and a preservative sold under the name UCARCIDE TM 250 available from Union Carbide Corporation. It should be understood that other preservatives would be equally applicable in the context of a pesticide composition formed in accordance with the present invention. When preservatives are used, they are generally present in an amount ranging from about 0.1 to about 5.0 wt. % based on the total weight of the pesticide composition. Preferably, the preservatives are present in an amount ranging from about 0.2 to about 2.0 wt. % based on the total weight of the pesticide composition.

Color additives may also be added to a pesticide composition formed in accordance with the present invention. Suitable color additives include those that tend to darken the color of the pesticide composition. Suitable colorants include charcoal, caramel coloring, and the like. Generally the colorant is added in a concentration that ranges from about 0.1 to about 2.0 wt. % based on the total weight of the pesticide composition.

A pH adjusting agent can also be an ingredient in a pesticide composition formed in accordance with the present invention. Control of the pH of the final product helps to optimize the effectiveness of the preservatives which tend to be most effective at a pH ranging from about 4.0 to about 4.5. Also, poisons such as metaldehyde have a tendency to break down at relatively high pHs; therefore, it is preferred to prevent this breakdown by maintaining the pH of the pesticide composition at a value below about 7.0. Preferably, the pH of the pesticide composition ranges from about 3.5 to 5.0. Conventional pH adjusting agents can be used to adjust the pH so long as the agent does not adversely affect or react with other components in the pesticide composition. Examples of suitable pH adjusting agents include conventional acids such as hydrochloric acid or phosphoric acid. Although the amount of the pH adjusting agent can vary over a wide range depending on the particular components used to formulate the pesticide composition when the preferred components are used as described above in their preferred amounts, it has been found that the pH adjusting agent can be used in an amount ranging from about 0.3 to about 3.0 wt. % based on the total weight of the pesticide composition. Preferably, the pH adjusting agent is used in an amount ranging from about 0.5 to about 1.5 wt. % based on the total weight of the pesticide composition.

It should be understood that given the ranges of components described above many different formulations of pesticide compositions can be provided in accordance with the present invention. Examples of specific formulations found to be effective for controlling molluscs are found in Table I below.

TABLE I

| EXEMPLARY PESTICIDE COMPOSITIONS | | | | | | |
|---|---|---|---|---|---|---|
| | Primary | FORMULATION | | | | |
| Component | Function | A | B | C | D | E |
| Water | Carrier | 78.9 | 74.4 | 73.95 | 74.2 | 74.2 |
| Metaldehyde | Poison | 4.0 | 4.0 | 4.0 | 4.0 | 4.0 |
| Malt Extract | Attractant | 7.0 | 5.0 | 5.0 | 5.0 | 5.0 |
| Bentonite Clay | Thickener | 5.5 | 2.0 | 2.0 | 2.0 | 2.0 |
| Xanthan Gum | Thickener | 0.8 | 0.2 | 0.2 | 0.2 | 0.2 |
| Corn Flour | Thickener | | 7.0 | 7.0 | 7.0 | 7.0 |
| Sodium Benzoate | Preservative | 3.0 | 1.0 | 1.0 | 1.0 | 1.5 |
| DANTOGARD TM | Preservative | | 1.5 | | | |
| Potassium Sorbate | Preservative | | | 1.0 | 1.0 | |
| Formaldehyde | Preservative | | | 0.25 | | |
| UCARCIDE TM 250 | Preservative | | | | | 0.5 |

TABLE I-continued

EXEMPLARY PESTICIDE COMPOSITIONS

| Component | Primary Function | FORMULATION | | | | |
|---|---|---|---|---|---|---|
| | | A | B | C | D | E |
| Charcoal | Colorant | 0.2 | 0.2 | 0.2 | 0.2 | 0.2 |
| Hydrochloric Acid | pH Adjustment | 0.6 | | | | |
| Phosphoric Acid | pH Adjustment | | 0.7 | 1.4 | 1.4 | 1.4 |
| POLYOL-P ™ | Humidifying Agt | | 4.0 | | | |
| d-Sorbitol | Humidifying Agt | | | 4.0 | 4.0 | 4.0 |

A pesticide composition formed in accordance with the present invention can be formulated by conventional mixing techniques such as a stirred tank or mixing vessel. An example of a procedure for mixing the individual components of the pesticide composition formed in accordance with the present invention includes the following steps:

1. Placing water in an appropriate mixing vessel.
2. Adding the attractant, blending and heating the composition to approximately 180° F. for about three minutes.
3. Adding the preservative to the hot mixture and stirring, slowly adding the thickener to the mixing vessel with constant stirring.
4. Adding the coloring agent to the vessel.
5. Adding the poison to the vessel with stirring. If metaldehyde is the poison, it is important to add the metaldehyde after any heating step that would cause the metaldehyde to vaporize.
6. If the thickening agent employed is heat activated, the contents of the vessel should be heated to obtain the desired viscosity.

Pesticide compositions formed in accordance with the present invention can be used by dispensing the composition directly to the area in which control of the particular pest is desired. The attractant in the pesticide composition will tend to attract pests to the composition. When the pests are molluscs such as slugs or snails, it is not necessary that the molluscs ingest the pesticide composition, substantial contact with the pesticide composition is normally sufficient to be fatal to the molluscs. In the context of insects and rodents, it may be necessary Wthat these pests ingest the composition in order for the composition to be lethal.

Pesticide compositions formed in accordance with the present invention are effective to control pests such as molluscs, insects, and small rodents without creating a substantial threat to other life. In addition, pesticide compositions formed in accordance with the present invention use a carrier that is substantially free of petroleum-based products such as oil that may contaminate the environment. The compositions are resistant to erosion by water and retain their moisture even after extended periods of exposure to moisture and sunlight. The following example is intended to illustrate the water resistance of a pesticide composition formed in accordance with the present invention and is not intended to limit the scope of disclosure described hereinabove.

EXAMPLE 1

Water Resistance

A pesticide composition including in wt. % based on the total weight of the pesticide composition 74.2% water, 5.0% malt extract, 7.0% corn flour, 2.0% bentonite clay, 0.2% xanthan gum, 4% d-sorbitol (70% solution), 1.4% phosphoric acid (80% technical), 1.5% sodium benzoate, 0.5% UCARCIDE ™ 250 preservative (50% technical), 4.0% metaldehyde, and 0.2% charcoal was formed by mixing the above ingredients as described in the specification. The resulting product had a consistency similar to mayonnaise and was black in color. A sample of the pesticide composition in the shape of a blob was placed in a vessel of water without agitation in order to observe the water resistance of the composition. After 24 hours in the water, the pesticide composition maintened substantially the same shape as when it was introduced into the water. After 48 hours the blob had dispersed substantially in the water.

The example illustrates the ability of a pesticide composition formed in accordance with the present invention to be resistant to erosion by extended periods of exposure to water.

The present invention has been described in relation to preferred embodiments. One of ordinary skill after reading the foregoing specification, will be able to effect various changes, substitutions of equivalents, and other alterations without departing from the broad concepts disclosed herein. It is therefore intended that the scope of Letters Patent granted herein will be limited only by the definition contained in the appended claims and equivalents thereof.

The embodiments of the invention in which an exclusive property or privilege is claimed are defined as follows:

1. A weather resistant molluscicide composition in the form of a uniformly dispersed mixture comprising:
   (a) an aqueous carrier;
   (b) a poison in an amount effective to kill molluscs that contact said molluscicide composition;
   (c) an attractant for molluscs;
   (d) a thickener for increasing the viscosity of the molluscicide composition; and
   (e) a humidifying agent.
2. The composition of claim 1, further comprising a preservative.
3. The composition of claim 1, further comprising a color additive.
4. The composition of claim 1, further comprising a pH adjusting agent for adjusting the pH of the molluscicide composition to a value at which the effectiveness of said poison is optimized.
5. The composition of claim 1, wherein said thickener is used in an amount effective to increase the viscosity of the molluscicide composition such that the molluscicide composition is non-leveling when applied to a horizontal surface.
6. The composition of claim 5, wherein the viscosity of the molluscicide composition is such that the application of pressure will cause the composition to flow.
7. The composition of claim 1, wherein said humidifying agent is present in an amount effective to stabilize the moisture content of said molluscicide composition after said molluscicide composition is applied.

8. The composition of claim 1, wherein said thickener is used in an amount effective to adjust the viscosity of said molluscicide composition such that the viscosity of said molluscicide composition ranges from about 6,000 centipoise to about 18,000 centipoise measured at about 20 degrees Celsius.

9. The composition of claim 7, wherein said humidifying agent is present in an amount ranging from about 3.0 to about 5.0 wt. % based on the total weight of said molluscicide composition.

10. The composition of claim 1, wherein said poison is present in an amount ranging from about 2.0 to about 10.0 wt. % based on the total weight of said molluscicide composition.

11. The composition of claim 10, wherein said poison is present in an amount ranging from 3.0 to 5.0 wt. % based on the total weight of said molluscicide composition.

12. The composition of claim 8, wherein said thickener is present in an amount ranging from about 3.0 to about 15.0 wt. % based on the total weight of said molluscicide composition.

13. The composition of claim 12, wherein said thickener is present in an amount ranging from about 5.0 to about 10.0 wt. % based on the total weight of said molluscicide composition.

14. The composition of claim 9, wherein said humidifying agent is selected from the group of alcohols consisting of polyhydric alcohols.

15. The composition of claim 14, wherein said humidifying agent is sorbitol.

16. The composition of claim 15, wherein said poison is metaldehyde.

17. The composition of claim 12, wherein said thickener is selected from the group of thickening agents consisting of alginates, silicas, celluloses, gums, starches, glycogen, and dextrins.

18. The composition of claim 1, wherein the composition is stable in water for up to 24 hours, said stability being evaluated by placing said composition in an unagitated bath of water at about room temperature and observing the period of time required to substantially disperse the composition.

19. The composition of claim 8, wherein said thickener is used in an amount effective to adjust the viscosity of said molluscicide composition such that the viscosity of said molluscicide composition ranges from about 8,000 centipoise to about 10,000 centipoise measured at about 20 degrees Celsius.

20. A weather resistant molluscicide composition in the form of a uniformly dispersed mixture comprising:
    (a) an aqueous carrier;
    (b) a poison being present in an amount ranging from about 3.0 to about 5.0 wt. % based on the total weight of said molluscicide composition;
    (c) an attractant for molluscs;
    (d) a thickener for increasing the viscosity of the molluscicide composition, said thickener being selected from the group of thickening agents consisting of alginates, silicas, celluloses, gums, starches, glycogen, and dextrins, said thickener being present in an amount ranging between about 5.0 and about 10.0 wt. % based on the total weight of the molluscicide composition; and
    (e) a humidifying agent selected from the group of alcohols consisting of polyhydric alcohols, said humidifying agent being present in an amount ranging between about 3.0 and about 5.0 wt. % based on the total weight of the molluscicide composition.

21. The composition of claim 20, wherein said poison is metaldehyde.

22. A weather resistant pesticide composition in the form of a uniformly dispersed mixture comprising:
    (a) an aqueous carrier;
    (b) a poison in an amount effective to kill pests that contact said pesticide composition;
    (c) an attractant for pests;
    (d) a thickener for increasing the viscosity of the pesticide composition; and
    (e) a humidifying agent.

23. The composition of claim 22, wherein said humidifying agent is used in an amount ranging from about 3.0 to 5.0 wt. % based on the total weight of the pesticide composition.

24. The composition of claim 22, wherein said thickener is used in an amount effective to increase the viscosity of the pesticide composition such that the pesticide composition is non-leveling when applied to a horizontal surface.

25. The composition of claim 24, wherein the viscosity of the pesticide composition is such that the application of pressure will cause the composition to flow.

26. A weather resistant molluscicide composition in the form of a uniformly dispersed mixture consisting essentially of:
    (a) an aqueous carrier;
    (b) a poison in an amount effective to kill molluscs that contact said molluscicide composition;
    (c) an attractant for molluscs;
    (d) a thickener for increasing the viscosity of the molluscicide composition; and
    (e) a humidifying agent.

27. The molluscicide composition of claim 26, wherein the composition is substantially free of petroleum based oils.

* * * * *

UNITED STATES PATENT AND TRADEMARK OFFICE
CERTIFICATE OF CORRECTION

PATENT NO. : 5,017,620
DATED : May 21, 1991
INVENTOR(S) : Grassman et al.

It is certified that error appears in the above-identified patent and that said Letters Patent is hereby corrected as shown below:

| COLUMN | LINE | |
|---|---|---|
| 1 | 50 | after "dilute the" insert --dry-- |
| 2 | 6-7 | "precipi-tion" should be --precipitation-- |
| 2 | 42 | "precipition" should be --precipitation-- |

Signed and Sealed this

Thirtieth Day of March, 1993

Attest:

STEPHEN G. KUNIN

Attesting Officer        Acting Commissioner of Patents and Trademarks